United States Patent
Hu et al.

(10) Patent No.: US 11,214,562 B2
(45) Date of Patent: Jan. 4, 2022

(54) CYCLOHEXYL BENZAMIDE COMPOUNDS

(71) Applicant: Eli Lilly and Company, Indianapolis, IN (US)

(72) Inventors: Zhi Long Hu, Shanghai (CN); Lian Zhu Liu, Shanghai (CN); Tianwei Ma, Carmel, IN (US); Mi Zeng, Shanghai (CN); Haizhen Zhang, Shanghai (CN)

(73) Assignee: ELI LILLY AND COMPANY, Indianapolis, IN (US)

( * ) Notice: Subject to any disclaimer, the term of this patent is extended or adjusted under 35 U.S.C. 154(b) by 537 days.

(21) Appl. No.: 16/316,167

(22) PCT Filed: Jul. 17, 2017

(86) PCT No.: PCT/CN2017/093093
§ 371 (c)(1),
(2) Date: Jan. 8, 2019

(87) PCT Pub. No.: WO2018/014800
PCT Pub. Date: Jan. 25, 2018

(65) Prior Publication Data
US 2021/0292302 A1 Sep. 23, 2021

(30) Foreign Application Priority Data

Jul. 22, 2016 (WO) ................ PCT/CN2016/091025

(51) Int. Cl.
*C07D 403/04* (2006.01)
*A61P 3/10* (2006.01)

(52) U.S. Cl.
CPC .............. *C07D 403/04* (2013.01); *A61P 3/10* (2018.01)

(58) Field of Classification Search
CPC .................................. C07D 403/04; A61P 3/10
See application file for complete search history.

(56) References Cited

FOREIGN PATENT DOCUMENTS

| WO | 2015/120768 A1 | 8/2015 |
| WO | 2015/120768 A1 | 8/2016 |
| WO | 2016/138821 A1 | 9/2016 |

OTHER PUBLICATIONS

Du, Xiaohui et al., Phenylalanine derivatives as GPR142 agonists for the treatment of type II diabetes, Bioorganic & Medicinal Chemistry Letters, vol. 22, pp. 6218-6223, Aug. 10, 2012.
International Search Report of PCT/CN2017/093093 dated Oct. 20, 2017.
Lizarzaburu, Mike, et al., Discovery and optimization of a novel series of GPR142 agonists for the treatment of type 2 diabetes mellitus, Bioorganic & Medicinal Chemistry Letters, vol. 22, pp. 594-5947, Jul. 23, 2012.
Written Opinion of the International Searching Authority for PCT/CN2017/093093 dated Oct. 9, 2017.

*Primary Examiner* — Tracy Vivlemore
*Assistant Examiner* — Ebenezer O Sackey
(74) *Attorney, Agent, or Firm* — Quarles & Brady LLP

(57) ABSTRACT

A compound of the Formula (1) is below provided where R1-R5 are as described in the description and each "*" represents a chiral center.

15 Claims, No Drawings

CYCLOHEXYL BENZAMIDE COMPOUNDS

This invention relates to a series of cyclohexyal benzamide compounds pharmaceutically acceptable salts thereof, and therapeutic uses thereof.

GPR142 is reported to be expressed in pancreatic cells and associated with the stimulation of insulin secretion under conditions of high blood glucose. Compounds that effectuate GPR142 agonism are desired.

Compounds reported to be GPR142 agonists are disclosed in M. Lizarzaburu, et al. "Discovery and Optimization of a novel series of GPR142 agonists for the treatment of type 2 diabetes," Bioorganic and Medicinal Chemistry Letters 22 (2012) 5942-5947. The compounds reported by Lizarzaburu are a series of phenylalanine related structures.

The present invention provides a compound of Formula 1:

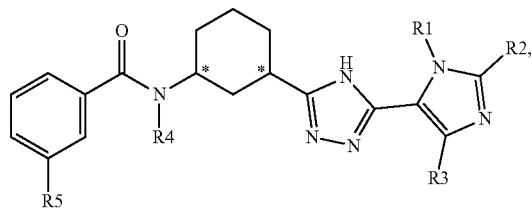

1 or a pharmaceutically acceptable salt thereof wherein * designates a chiral center; R1 is selected from: H, —CH₃, —CH₂CH₂OCH₃, and —CH₂CHF₂; R2 is selected from H and CH₃, or R1 and R2 can join to form a fused 6 membered heterocyclic ring containing O and the N bonded to R1; R3 is H or —CH₃; R4 is H or —CH₃; and R5 is selected from: Cl, —CF₃, and —OCF₃; or The * symbols in Formula 1 designates the chiral centers. The individual carbon of the chiral center at positions 1 and 3 on the cyclohexane ring can exhibit either the R or S configuration. Preferred compounds of the present invention have the benzamide attached to the carbon at the 4 position and the triazolyl ring attached to the carbon at the 2 position of the tetrahydropyranyl ring in a cis configuration relative to each other as illustrated in Formula 2.

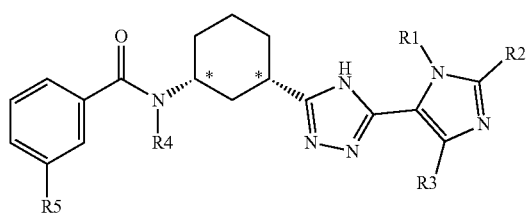

2

In another form, the present invention provides a compound of the Formula 2, or a pharmaceutically acceptable salt thereof, where "*" designates a chiral center and the substituents attached to the two chiral centers are cis relative to each other; R1 is selected from: H, —CH₃, —CH₂CH₂OCH₃, and —CH₂CHF₂; R2 is selected from H and CH₃, or R1 and R2 can join to from a fused 6 membered heterocyclic ring containing 0 and the N bonded to R1; R3 is H or —CH₃; R4 is H or —CH₃; and R5 is selected from: Cl, —CF₃, and —OCF₃. In preferred embodiments R1 is selected from —CH₃, —CH₂CH₂OCH₃, and —CH₂CHF₂. In still more preferred embodiments, R1 is —CH₃.

In another form, the present invention provides a compound according to Formula 1 or 2, or a pharmaceutically acceptable salt thereof, where R1 and R2 combine to form a fused 6 membered heterocyclic ring containing 0 and the N attached to R1.

In another form, the present invention provides a compound according to Formula 1 or 2, or a pharmaceutically acceptable salt thereof, wherein R2 is CH₃. In certain embodiments, R1 is s selected from: H, —CH₃, —CH₂CH₂OCH₃, and —CH₂CHF₂. In other embodiments, R1 is —CH₃. In preferred embodiments, R3 can be H; R4 can be H or —CH₃; and R5 can be selected from: Cl, —CF₃, and —OCF₃.

In another form, the present invention provides a compound according to Formula 1 or 2, or a pharmaceutically acceptable salt thereof, wherein R2 is H. In certain embodiments, R1 is s selected from: H, —CH₃, —CH₂CH₂OCH₃, and —CH₂CHF₂. In other embodiments, R1 is —CH₃. In preferred embodiments, R3 can be —CH₃; R4 can be H or —CH₃; and R5 can be selected from: Cl, —CF₃, and —OCF₃.

In another form, the present invention provides a compound according to Formula 1 or 2, or a pharmaceutically acceptable salt thereof, where R3 is —CH₃. In certain embodiments, R1 can be selected from: —CH₃, —CH₂CH₂OCH₃, and —CH₂CHF₂; more preferably R1 can be —CH₃; R2 can be H or CH₃; R4 can be H or —CH₃; and R5 can be selected from: Cl, —CF₃, and —OCF₃.

In another form, the present invention provides a compound according to Formula 1 or 2, or a pharmaceutically acceptable salt thereof, wherein R4 is —CH₃. In certain embodiments, R1 is s selected from: —CH₃, —CH₂CH₂OCH₃, and —CH₂CHF₂. In other embodiments, R1 is —CH₃. In other embodiments R2 is H; and R5 can be selected from: Cl, —CF₃, and —OCF₃.

In another form, the present invention provides a compound according to Formula 1 or 2, or a pharmaceutically acceptable salt thereof, where R5 is Cl or —OCF₃. Preferably, R5 is Cl; R1 is s selected from: —CH₃, —CH₂CH₂OCH₃, and —CH₂CHF₂. In other embodiments, R1 is —CH₃. In other embodiments R2 is H; R3 is H, and R4 is —CH₃.

In another form, the present invention provides a compound of the Formula 3:

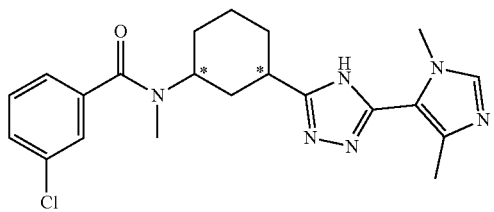

3 wherein * designates a chiral center, or a pharmaceutically acceptable salt thereof.

In yet another form, the present invention provides a compound of the Formula 4, or pharmaceutically acceptable salt thereof:

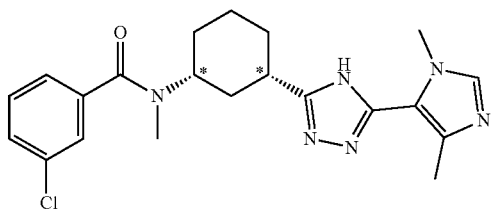

4 wherein * designates a chiral center and the substituents attached to the chiral centers are cis relative to each other. In one embodiment, the compound of Formula 4 is provided as a free base.

In another form, the present invention provides a pharmaceutical composition comprising a compound according to any one of Formulae 1 to 4, or a pharmaceutically acceptable salt thereof, and at least one of a pharmaceutically acceptable carrier, diluent, or excipient.

In another form, the present invention provides a method for treating a patient in need of treatment for type II diabetes, comprising administering to the patient an effective amount of a pharmaceutically acceptable composition that includes a compound according to any one of Formulae 1 to 4 or a pharmaceutically acceptable salt thereof.

In another form, the present invention provides a method for treating a patient in need of treatment for type II diabetes, comprising administering to the patient an effective amount of a compound according to any one of Formulae 1 to 4 or a pharmaceutically acceptable salt thereof.

In another form, the present invention provides a compound, or a pharmaceutically acceptable salt thereof, according to any one Formula 1 to 4 for use in therapy.

In another form, the present invention provides a compound, or a pharmaceutically acceptable salt thereof, according to any one Formula 1 to 4 for use in therapy to treat type II diabetes.

In another form, the present invention provides for the use of a compound, or a pharmaceutically acceptable salt thereof, according to any one Formula 1 to 4 in the manufacture of a medicament.

In another form, the present invention provides for the use of a compound, or a pharmaceutically acceptable salt thereof, according to any one Formula 1 to 4 in the manufacture of a medicament for the treatment of type II diabetes.

The present invention can also include a compound according to Formulae 1 to 4 and a second pharmaceutically active agent. The second pharmaceutically active agent is suitable for administration sequentially, simultaneously, or concomitantly in combination with a GPR142 agonist. In an embodiment, the second pharmaceutical agent is an agent effective for treating diabetes. In another embodiment, the second pharmaceutical agent is, for example, metformin.

Compounds of the present invention are GPR142 agonists, and the invention contemplates methods for treating a disease or condition associated with a decrease in GPR142. Compounds of the present invention according to any one of Formulae 1 to 4, or a pharmaceutically acceptable salt thereof, may be useful in the treatment of a disease or condition associated with the modulation of GPR142.

As used herein, the terms "treating", "to treat", or "treatment", includes slowing, reducing, or reversing the progression or severity of an existing symptom, disorder, condition, or disease, which can include treating diabetes and preferably type II diabetes.

As used herein, the term "patient" refers to a mammal, fowl, or fish. Preferably, the patient is a human or companion mammal, such as, a dog or cat or other domesticated mammal, such as, a cow, pig, horse, sheep, rabbit, and goat; or other livestock, such as, fowl or fish.

As used herein, the term "effective amount" refers to the amount or dose of a compound of the invention or a pharmaceutically acceptable salt thereof, which upon single or multiple dose administration to the patient, provides the desired effect in the mammal. It will be understood that the amount of active agent actually administered will be determined by a physician or veterinarian, in light of the relevant circumstances, including the condition to be treated, the chosen route of administration, the actual active agent administered, the age, weight, and response of the individual patient, and the severity of the symptoms and other relevant circumstances. In one example, the effective amount may be the amount of a compound of the invention effective to lower blood or plasma glucose levels.

The compounds of the present invention can be provided as a pharmaceutically acceptable salt. "Pharmaceutically-acceptable salt" refers to salts of a compound of the invention considered to be acceptable for clinical and/or veterinary use. Examples of pharmaceutically acceptable salts and methodologies for preparing them can be found in P. Stahl, et al., Handbook of Pharmaceutical Salts: Properties, Selection and Use, (VCHA/Wiley-VCH, 2002) and S. M. Berge, et al., "Pharmaceutical Salts," *Journal of Pharmaceutical Sciences*, Vol. 66, No. 1, January 1977.

The term "pharmaceutically acceptable carrier, diluent, or excipient" means that the carrier, diluent, and excipient are pharmaceutically compatible with the other ingredients of the composition. Pharmaceutical compositions and processes for their preparation are known and examples can be found in "Remington: The Science and Practice of Pharmacy", A. Gennaro, et al. Eds. 21st Ed., Mack Publishing Co., 2005. Non-limiting examples of pharmaceutically acceptable carriers, diluents, and excipients include the following: saline, water, starch, sugars, mannitol, and silica derivatives; binding agents such as carboxymethyl cellulose and other cellulose derivatives, alginates, gelatin, and polyvinyl-pyrrolidone; kaolin, bentonite; and polyethyl glycols.

Individual isomers, enantiomers, and diastereomers may be separated or resolved at any convenient point in the synthesis of compounds listed below. (See for example, J. Jacques, et al., "Enantiomers, Racemates, and Resolutions", John Wiley and Sons, Inc., 1981, and E. L. Eliel and S. H. Wilen, *Stereochemistry of Organic Compounds*", Wiley-Interscience, 1994). Additionally, the intermediates described in the following Schemes, Preparations, and Examples contain a number of nitrogen, hydroxy, and acid protecting groups such as esters. The protecting group may be the same or different in each occurrence depending on the particular reaction conditions and the particular transformations to be performed. The protection and deprotection conditions are known and are described in the literature. (See for example, Greene and Wuts, Protective Groups in Organic Synthesis, (T. Greene and P. Wuts, eds., 2d ed. 1991).

The compounds of the present invention, or salts thereof, may be prepared by a variety of procedures known to one of ordinary skill in the art, some of which are illustrated in the schemes, preparations, and examples below. One of ordinary skill in the art recognizes that the specific synthetic steps for each of the routes described may be combined in different ways, or in conjunction with steps from different schemes, to prepare compounds of the invention, or salts thereof. The products of each step in the schemes below can be recovered by conventional methods well known in the art, including extraction, evaporation, precipitation, chromatography, filtration, trituration, and crystallization. In the schemes below, all substituents unless otherwise indicated, are as previously defined. The reagents and starting materials are readily available to one of ordinary skill in the art.

The abbreviations used herein are defined according to Aldrichimica Acta, Vol. 17, No. 1, 1984. Other abbreviations are defined as follows: "AUC" refers to area under the curve; "BSA" refers to Bovine Serum Albumin; "Burgess reagent" refers to methyl N-(triethylammoniumsulfonyl) carbamate; "CDI" refers to 1,1'-carbonyldiimidazole; "DCC" refers to 1,3-dicyclohexylcarbodiimide; "DCM" refers to dichloromethane or methylene chloride; "DEAD" refers to diethyl azodicarboxylate; "DIAD" refers to diisopropyl azodicarboxylate; "DIC" refers to 1,3-diisopropylcarbodiimide; "DiPEA" refers to ethyldiisopropal amine; "DMAP" refers to dimethylaminopyridine; "DMEM" refers to Dulbecco's Modified Eagle's Medium; "$EC_{50}$" refers to the effective concentration at half the maximal response; "$ED_{50}$", refers to the effective dose in milligrams per kilogram ("mpk") for 50% of subjects receiving the test compound; "EDCI" refers to 1-(3-dimethylaminopropyl)-3-ethylcarbodiimide hydrochloride; "ee" refers to enantiomeric excess; "FBS" refers to Fetal Bovine Serum; "HATU" refers to (1-[bis(dimethylamino)methylene]-1H-1,2,3-triazolo[4,5-b]pyridinium 3-oxid hexafluorophosphate); "HBSS" refers to Hank's Balanced Salt Solution; "HBTU" refers to (1H-benzotriazol-1-yloxy)(dimethylamino)-N,N-dimethylmethaniminium hexafluorophosphate; "HEK" refers to human embryonic kidney; "HEPES" refers to 4-(2-hydroxyethyl)-1-piperazineethanesulfonic acid; "HOAt" refers to 1-hydroxy-7-azobenzotriazole; "HOBt" refers to 1-hydroxylbenzotriazole hydrate; "HPLC" refers to high-performance liquid chromatography; "hr or hrs" refers to hour or hours; "HTRF®" refers to homogeneous time resolved fluorescence; "IP-1" refers to Inositol phosphate-1; "IPGTT" refers to intraperitoneal glucose tolerance tests; "MeOH" refers to methyl alcohol or methanol; "min" refers to minutes; "PG" refers to protecting group; "Ph" refers to phenyl; "PyBOP" refers to (benzotriazol-1-yl-oxytripyrrolidinophosphonium hexafluorophosphate); "PyBrOP" refers to bromo(tri-pyrrolidinyl)phosphonium hexafluorophosphate; "rt" or "RT" refers to room temperature; "TEA" refers to triethylamine and "THF" refers to tetrahydrofuran.

Scheme 1

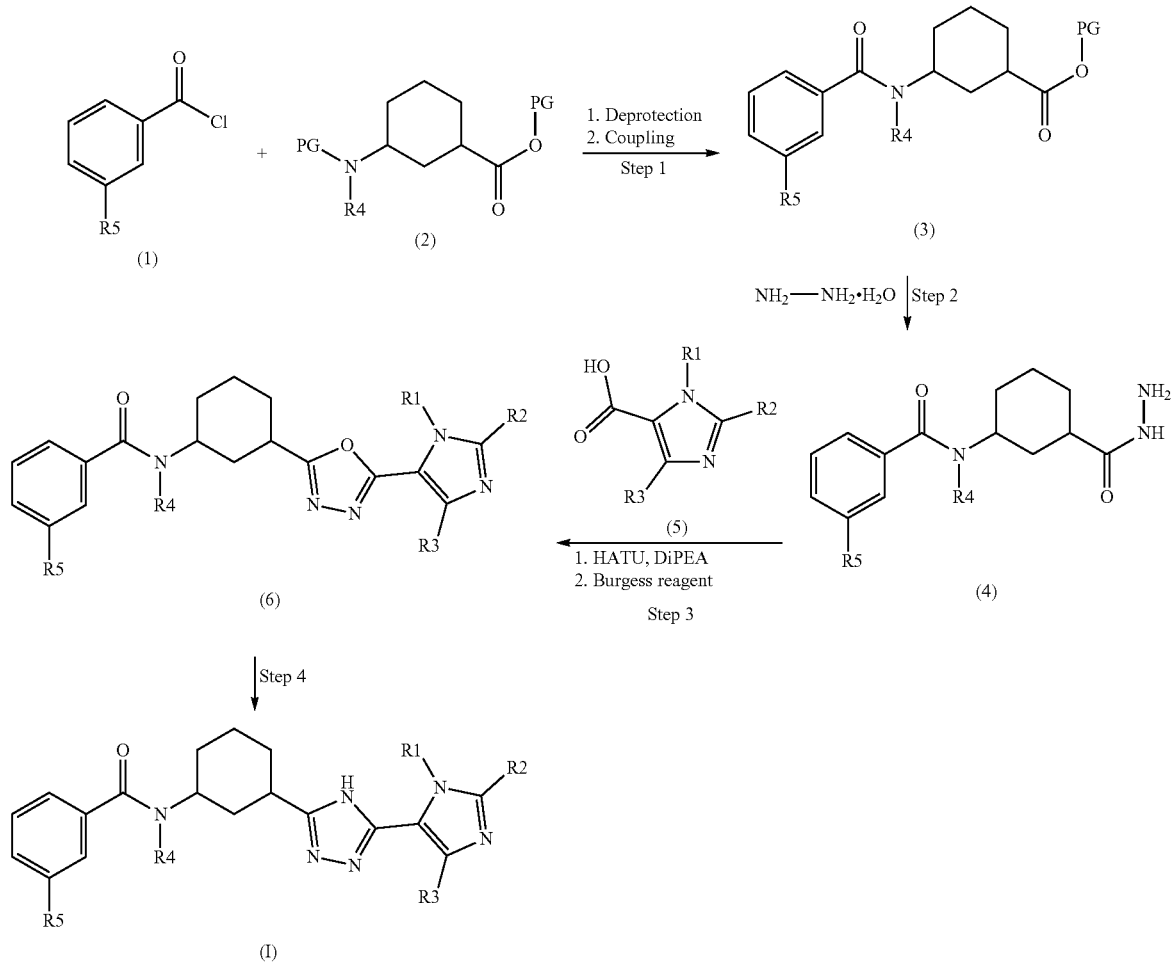

In Scheme 1, step 1, substep 1, a protected amine can be deprotected by an acid such as TFA. In substep 2, step 1, a nucleophilic addition with an aryl acyl chloride (1) and an amine-cyclohexyl-protected carboxylate (2) can be accomplished using an organic base such as TEA in solvents such as DCM or THF and a temperature ranging from about 0° C. to rt to give compound (3) The resulting protected carboxylate (3) can be treated with hydrazine monohydrate in an alcohol solvent, such as ethanol, to give the hydrazine carbonyl compound (4) of step 2. In scheme 1, the term "PG" is a carboxylic acid protecting group. Alternatively, a protected carboxylate can be treated with hydrazine monoin place of the more traditional coupling reagents or in place of HATU. An additive such as DMAP may be used to improve the reaction. The intermediate can be purified via silica gel chromatography and used directly in substep 2. The carbohydrazide intermediate of step 3, substep 1 can be treated with Burgess reagent resulting in an acylation dehydration to form an oxadizole (6), the product of step 3. In step 4, the oxadizole (6) can be converted to a triazole using ammonium acetate in an acid such as acetic acid and heating to about 150-160° C. under microwave conditions to give compounds of Formula I.

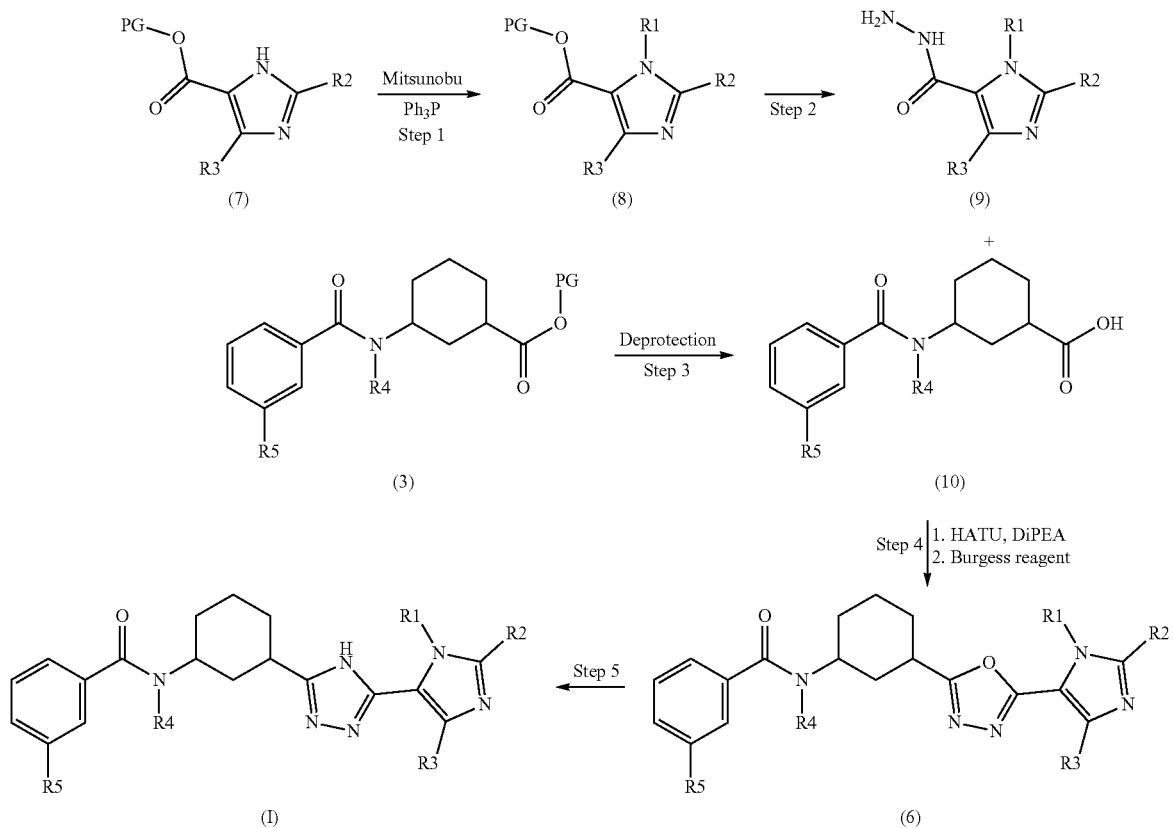

Scheme 2 hydrate in to give the hydrazine carbonyl compound of step 2. In step 3, an amide coupling can be accomplished in substep 1 with the hydrazine of compound (4) and the carboxylic acid of the substituted imidazole (5) using an organic base such as DiPEA and a reagent such as HATU. HATU is used as a coupling reagent to generate an active ester from the carboxylic acid (5). There are a number of methods and reagents for amide formation resulting from the reaction of carboxylic acids and amines. For example, the reaction of the amine compound with an appropriate carboxylic acid in the presence of a coupling reagent with or without an organic base such as DiPEA or TEA can provide the desired compound. Coupling reagents include carbodiimides, such as DCC, DIC, EDCI or a carbonyldiimidazole such as CDI. Amide coupling additives, such as HOBt and HOAt can also be used to enhance the reaction. Additionally, uronium or phosphonium salts of non-nucleophilic anions, such as HBTU, PyBOP, and PyBrOP could be used Alternatively, in Scheme 2, the protected carboxylic acid, (8) of compound 5 can be prepared from a Mitsunobu reaction as shown in step 1. Mitsunobu reactions can involve the alkylation of an amine (7) with an alcohol using triphenylphosphine and an azodicarboxylate such as DIAD or DEAD in a solvent such as THF to give (8), the product of step 1. Compound (8) can be converted to a carbohydrazide with hydrazine monohydrate as described in Scheme 1, step 2 to give compound (9). Compound (3), Scheme 1, a protected carboxylic acid can be deprotected under conditions well known by one skilled in the art using a base such as sodium hydroxide to give compound (10) in step 3. An amide coupling of Compounds (10) and (9) can be completed as described for Scheme 1, substep 1, step 3 and further reacted with Burgess reagent as described in Scheme 1, substep 2, step 3 to give compound (6) in Scheme 2, step 3 which can then be converted to compounds of Formula I (step 5) as described in Scheme 1, step 4.

Scheme 3

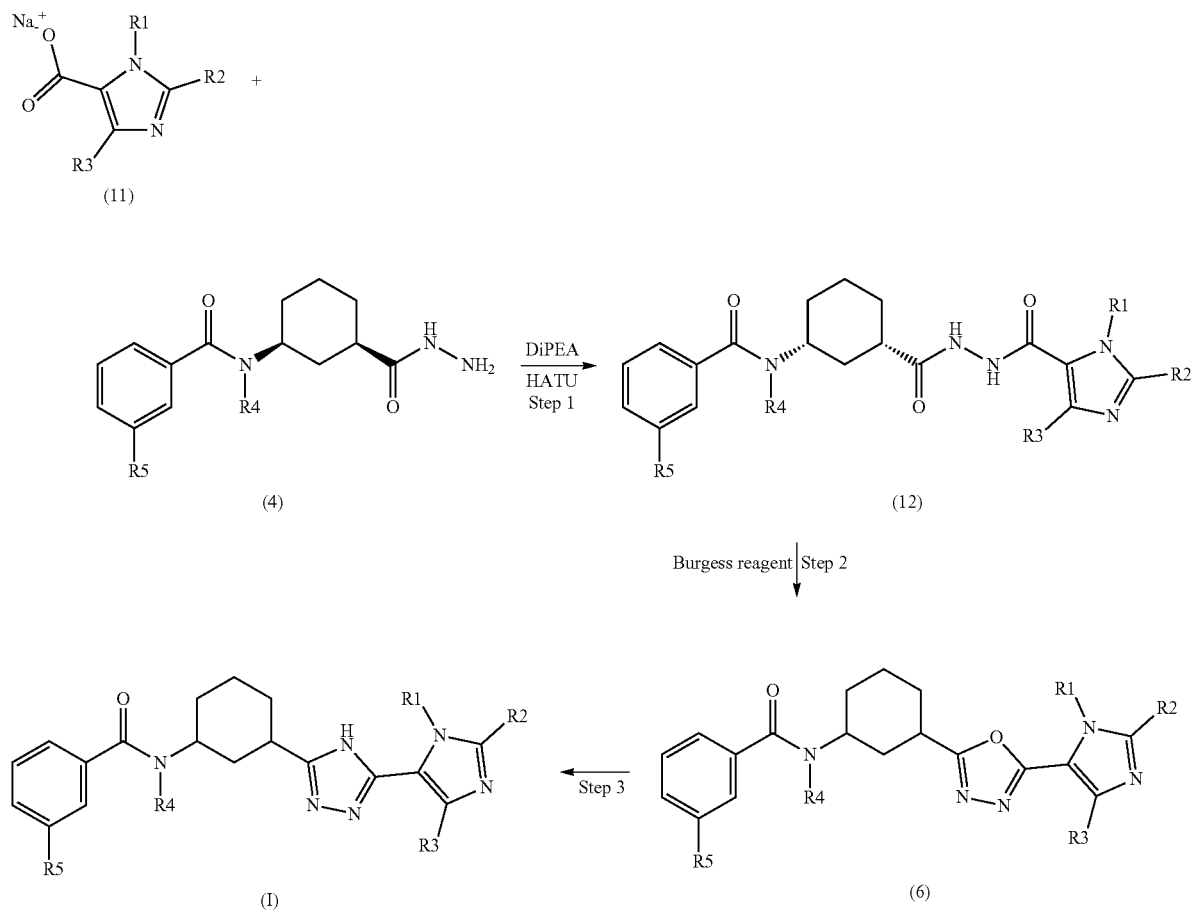

In another alternative method, as shown in Scheme 3, the salt of the carboxylate (11) can be coupled with the carbohydrazide (4) in step 1 to give compound (12) using the coupling conditions as, for example, described in Scheme 1, substep 1, step 3. In step 2, the carbohydrazide can be treated with Burgess reagent as described in Scheme 1, substep 2, step 3 to give the oxadiazole (6) and then compounds of Formula I (step 3) can be formed as described in Scheme 1, step 4.

A pharmaceutically acceptable salt of the compounds of the invention, such as a hydrochloride salt, can be formed, for example, by reaction of an appropriate free base of Formula I, an appropriate pharmaceutically acceptable acid such as hydrochloric acid in a suitable solvent such as diethyl ether under standard conditions known in the art. Additionally, the formation of such salts can occur simultaneously upon deprotection of a nitrogen protecting group. See, for example, Gould, P. L., "Salt selection for basic drugs," *International Journal of Pharmaceutics*, 33: 201-217 (1986); Bastin, R. J., et al. "Salt Selection and Optimization Procedures for Pharmaceutical New Chemical Entities,"

The following Preparations and Examples further illustrate the invention and represent typical synthesis of the compounds of formulae.

Add trifluoroacetic acid (21.26 mL, 281.2 mmol) to a solution of methyl (1S,3R)-3-[tert-butoxycarbonyl(methyl)amino]cyclohexanecarboxylate (25.44 g, 93.74 mmol) in DCM (10 mL) at rt. Stir the mixture at rt for 24 hrs. Add DCM (200 mL), water (200 mL) and then a NaOH (4 M) solution to adjust the pH to 9-10. Collect the organic layer. Wash the organic layer with H$_2$O, dry over anhydrous Na$_2$SO$_4$, filter, and concentrate the filtrate to give the title compound (16 g, 99.68%) as a light solid. MS (m/z): 172 (M+1).

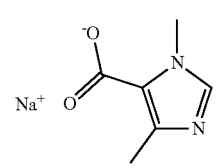

Add NaOH (0.451 g, 10.7 mmol) to a solution of ethyl 3,5-dimethylimidazole-4-carboxylate (1.00 g, 5.35 mmol) in EtOH (5 mL) and water (5 mL). Stir the reaction mixture at 60° C. for 1 hr. Concentrate the solution to give the title compound (0.960 g, 99.6%) as a yellow solid. LC/MS (m/z): 141 (M−21).

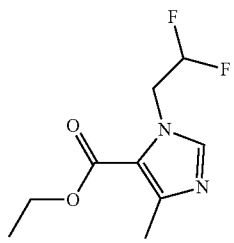

Add DIAD (2.01 g, 9.74 mmol) dropwise at 0-5° C. under nitrogen followed by 2,2-difluoroethanol (0.64 g, 7.79 mmol) to a stirring solution of ethyl 4-methyl-1H-imidazole-5-carboxylate (1.00 g, 6.49 mmol) and triphenylphosphine (2.60 g, 9.71 mmol) in THF (20 mL). Stir the mixture at 10-15° C. for 16 hrs. Concentrate the mixture and purify by silica gel combi-flash chromatography eluting with EtOAc in PE from 10% to 35% to give the title compound (0.47 g, 33.2%) as yellow oil. LC/MS (m/z): 219 (M+H).

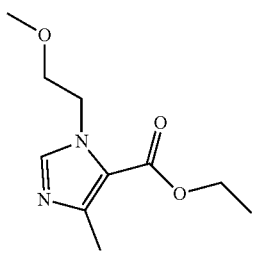

Add DEAD (9.58 g, 55.0 mmol) in THF (10 mL) slowly over 10 min to a solution of ethyl 4-methyl-1H-imidazole-5-carboxylate (7.71 g, 50.0 mmol), DiPEA (8.7 mL, 50.0 mmol), 2-methoxyethanol (4.57 g, 60.0 mmol) and triphenylphosphine (14.9 g, 55.0 mmol) in THF (130 mL) at 0° C. Warm the mixture to room temperature and stir for 3 days. Concentrate the mixture and dilute with Et₂O (80 mL). Filter the mixture and dilute with Et₂O (100 mL). Wash with water (100 mL) and concentrate to dryness. Purify the residue via silica gel flash chromatography eluting with 1/1 EtOAc/hexanes followed by 1/20 MeOH/DCM to give the title compound (8.3 g, 78%). MS (m/z): 213 (M+H).

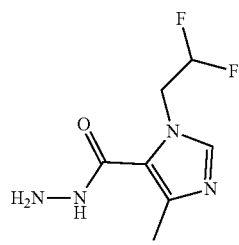

Heat a mixture of ethyl 3-(2,2-difluoroethyl)-5-methyl-imidazole-4-carboxylate (0.470 g, 2.15 mmol) and hydrazine monohydrate (1.08 g, 21.54 mmol) in EtOH (3 mL) at 110° C. under microwave conditions for 5 hrs. Concentrate the reaction mixture and dry it in vacuo to give the title compound (0.469 g, 70.4%, 66% purity) as a white solid. LC/MS (m/z): 205 (M+H).

Prepare the following compound essentially as described for Preparation 5 using the appropriate ester.

| Prep. | Chemical Name | Structure | ES/MS (m/z) (M + H) |
|---|---|---|---|
| 6 | 3-(2-Methoxyethyl)-5-methyl-imidazole-4-carbohydrazide | 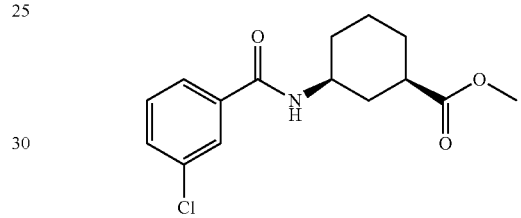 | 199 |

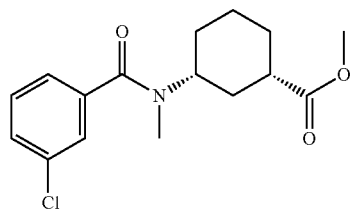 [SMILES: COC(=O)[C@H]1CCC[C@@H](N(C)C(=O)c2cccc(Cl)c2)C1]

Add 3-chlorobenzoyl chloride (2.43 mL, 18.8 mmol) dropwise to a mixture of methyl (racemic)-3-aminocyclohexanecarboxylate;hydrochloride (2.70 g, 12.5 mmol) and trimethylamine (5.30 mL, 37.6 mmol) in DCM (30 mL) at 0° C. Stir the mixture at 25° C. for 1 hr. Dilute the reaction mixture with DCM (20 mL) and wash with aq Na₂CO₃ (2×20 mL) and brine (20 mL). Dry over Na₂SO₄, filter, and concentrate under reduced pressure. Purify the residue by silica gel column chromatography eluting with 40% EtOAc in PE to give the title compound (3.60 g, 87.3%) as a white solid. LC/MS (m/z): 296 (M+H).

Add TEA (15.6 mL, 112.1 mmol) and 3-chlorobenzoyl chloride (18.0 g, 102.8 mmol) to a solution of methyl (1S,3R)-3-(methylamino) cyclohexanecarboxylate (16.00 g, 93.44 mmol) in DCM (150 mL) at 0° C. Warm the mixture to rt and stir for 2 hrs. Wash the mixture with H₂O (2×100 mL). Collect the organic layer, dry over anhydrous Na₂SO₄, filter, and evaporate the solvent from the filtrate in vacuo to give a residue. Subject the residue to silica gel flash chromatography eluting with a gradient of 0-35% EtOAc/hexanes to give the title compound (17.16 g, 54.54%) as a light yellow oil. MS (m/z): 332 (M+23).

Prepare the following compound essentially as described for Preparation 8 using the appropriate benzoyl chloride.

| Prep | Chemical Name | Structure | ES/MS (m/z) (M + H) |
|---|---|---|---|
| 9 | Cis-chiral-(1S,3R)-3-[Methyl-[3-(trifluoromethyl)benzoyl]amino]cyclohexanecarboxylate | 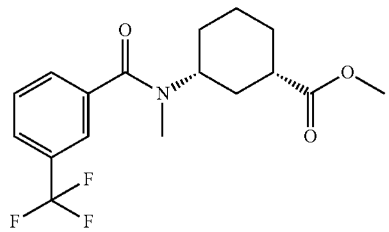 [SMILES: COC(=O)[C@H]1CCC[C@@H](N(C)C(=O)c2cccc(C(F)(F)F)c2)C1] | 344.35 |

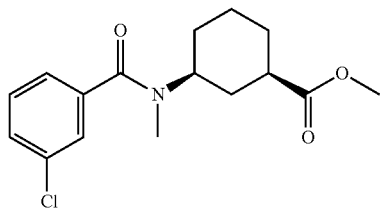 [SMILES: COC(=O)[C@@H]1CCC[C@H](N(C)C(=O)c2cccc(Cl)c2)C1]

Add TEA (0.89 g, 8.8 mmol, 3.0 equiv.) to a solution of methyl (1R,3S)-3-(methylamino)cyclohexanecarboxylate (0.50 g, 2.9 mmol) in DCM (25 mL) at 0° C. Add 3-chlorobenzoyl chloride (0.51 g, 2.9 mmol, 1.0 equiv.) and stir the mixture at 0° C. for 1 hr. Wash the mixture with water (2×15 mL), separate, dry the organic layer, and concentrate to dryness to give the title compound (0.90 g, 100%). MS (m/z): 310 (M+1).

Add hydrazine monohydrate (5 mL) to a stirring solution of cis-racemic-methyl-3-[(3-chlorobenzoyl)amino]cyclohexanecarboxylate (1.00 g, 3.04 mmol) in EtOH (20.0 mL) at 15° C. Remove the EtOH under vacuo and add DCM (200 mL) and MeOH (20 mL). Wash the organic layer with water (50 mL) and brine (50 mL). Dry the organic solution over anhydrous sodium sulfate and concentrate to give the title compound (1.00 g, 100%) as a white solid. LC/MS (m/z): 296 (M+H).

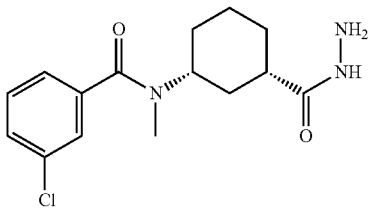

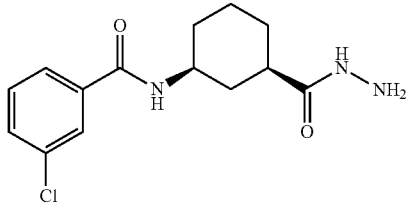 [SMILES: NNC(=O)[C@@H]1CCC[C@H](NC(=O)c2cccc(Cl)c2)C1]

Heat a mixture of methyl (1S,3R)-3-[(3-chlorobenzoyl)-methyl-amino]cyclohexanecarboxylate (10.0 g, 32.3 mmol) and hydrazine monohydrate (15 mL) in MeOH (40 mL) at 70° C. for 2 hrs. Concentrate the mixture to provide a residue. Collect and dry the residue to give the title compound (10.0 g, 100%). MS (m/z): 310 (M+1).

Prepare the following compound essentially as described for Preparation 12 using the appropriate ester.

| Prep | Chemical Name | Structure | ES/MS (m/z) (M + H) |
|---|---|---|---|
| 13 | Cis-chiral-N-[(1R,3S)-3-(Hydrazinecarbonyl)cyclohexyl]-N-methyl-3-(trifluoromethyl)benzamide | 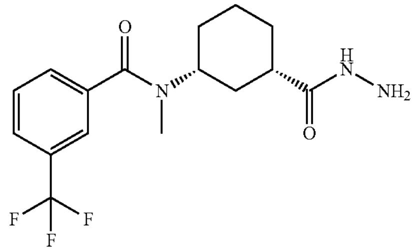 [SMILES: CN(C(=O)c1cccc(C(F)(F)F)c1)[C@@H]1CCC[C@H](C(=O)NN)C1] | 344.15 |

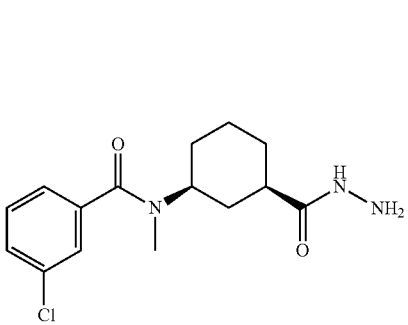 [SMILES: CN(C(=O)c1cccc(Cl)c1)[C@H]1CCC[C@@H](C(=O)NN)C1]

Heat a solution of methyl (1R,3S)-3-R3-chlorobenzoyl)-methyl-aminolcyclohexanecarboxylate (0.85 g, 2.7 mmol) and hydrazine monohydrate (1.4 g, 27 mmol, 10 equiv.) in EtOH (10 mL) at 85° C. for 3 hrs. Concentrate the mixture and dry it in vacuo to give the title compound (0.85 g, 100%). MS (m/z): 310 (M+1).

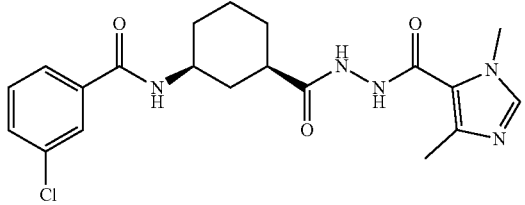 [SMILES: Cc1ncn(C)c1C(=O)NNC(=O)[C@@H]1CCC[C@H](NC(=O)c2cccc(Cl)c2)C1]

Add EDCI (0.630 g, 3.29 mmol) and HOBt (0.444 g, 3.29 mmol) to a stirring solution of sodium; 3,5-dimethylimidazole-4-carboxylate (0.466 g, 2.88 mmol) in DMF (25 mL) at 15° C. Stir for 0.5 hr and add 4-methylmorpholine (0.831 g, 8.22 mmol) and cis-racemic-3-chloro-N-[3-(hydrazinecarbonyl)cyclohexyl]benzamide (0.900 g, 2.74 mmol). Stir the mixture at 15° C. for 1 hr. Add H₂O (100 mL) to the solution and then extract the aqueous phase with DCM (3×100 mL). Combine the organic extracts, dry the solution over Na₂SO₄, filter the mixture, and concentrate the mixture to dryness to give the title compound (1.20 g, 94.4%) as a yellow solid. LC/MS (m/z): 418 (M+H).

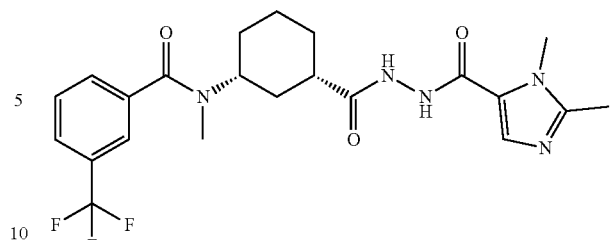

Add DiPEA (1.21 mL, 6.931 mmol) to a mixture of N-[(1R,3S)-3-(hydrazinecarbonyl)cyclohexyl]-N-methyl-3-(trifluoromethyl)benzamide (2.069 g, 2.772 mmol), 2,3-dimethylimidazole-4-carboxylic acid: hydrochloride (0.510 g, 2.310 mmol), and HATU (1.165 g, 3.003 mmol) in THF (20 mL). Stir the mixture at rt for 1 hr and at 60° C. for 3 hrs. Concentrate the mixture and purify the residue via silica gel flash chromatography eluting with 0-5% MeOH/DCM to give the title compound (0.539 g, 37.6%) as a white solid. LC/MS (m/z)=466 (M+H).

Prepare the following compound essentially as described for Preparation 16 using the appropriate carboxylic acid.

| Prep. | Chemical Name | Structure | ES/MS (m/z) (M + H) |
|---|---|---|---|
| 18 | Cis-chiral-N-methyl-N-[(1R,3S)-3-[[(2-methyl-1H-imidazole-5-carbonyl)amino]carbamoyl]cyclohexyl]-3-(trifluoromethyl)benzamide | 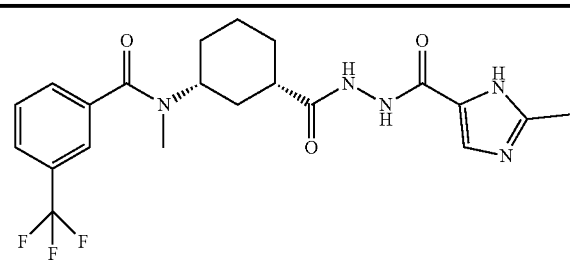 | 452 |

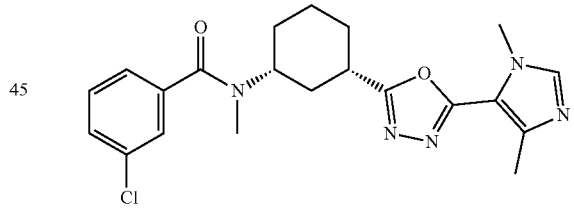

Add DiPEA (4.8 g, 37 mmol, 3.0 equiv) to 3-chloro-N-[(1R,3S)-3-(hydrazinecarbonyl)cyclohexyl]-N-methyl-benzamide (3.8 g, 12 mmol), 3,5-dimethylimidazole-4-carboxylic acid (1.7 g, 12 mmol, 1.0 equiv.), and HATU (6.7 g, 17 mmol, 1.4 equiv.) in THF (100 mL). Stir the mixture at rt for 4 hrs. Concentrate the mixture to provide a residue. Subject the residue to silica gel flash chromatography eluting with 10:1 DCM/MeOH to give the desired crude intermediate. Add THF (100 mL) to the crude intermediate followed by Burgess reagent (8.0 g, 33 mmol). Stir the mixture at rt for 4 hrs and then heat to 45° C. for 30 min Concentrate the mixture to provide a residue. Subject the residue to silica gel flash chromatography eluting with a gradient of 0 to about 10% MeOH/DCM to give the title compound (2.08 g, 41%). MS (m/z): 414 (M+1).

Prepare the following compounds essentially as described for Preparation 19 using the appropriate carboxylic acid.

| Prep | Chemical Name | Structure | ES/MS (m/z) (M + H) |
|---|---|---|---|
| 20 | Cis-chiral-3-Chloro-N-methyl-N-[(1R,3S)-3-[5-(4-methyl-1H-imdazol-5-yl)-1,3,4-oxadiazol-2-yl]cyclohexyl]benzamide | 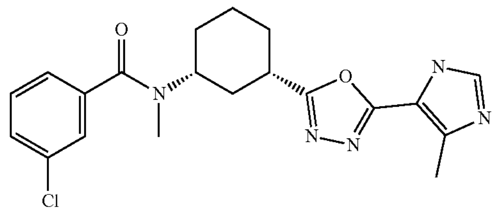 [SMILES: Cc1nc[nH]c1-c1nnc([C@H]2CCC[C@@H](N(C)C(=O)c3cccc(Cl)c3)C2)o1] | 400 |
| 21 | Cis-chiral-3-Chloro-N-[(1R,3S)-3-[5-(2,3-dimethylimidazol-4-yl)-1,3,4-oxadiazol-2-yl]cyclohexyl]-N-methyl-benzamide | 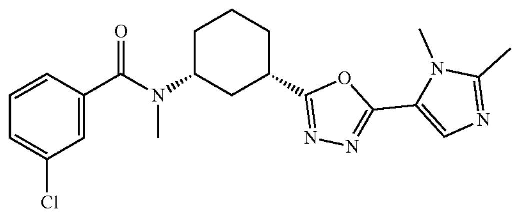 [SMILES: Cc1ncc(-c2nnc([C@H]3CCC[C@@H](N(C)C(=O)c4cccc(Cl)c4)C3)o2)n1C] | 414 |

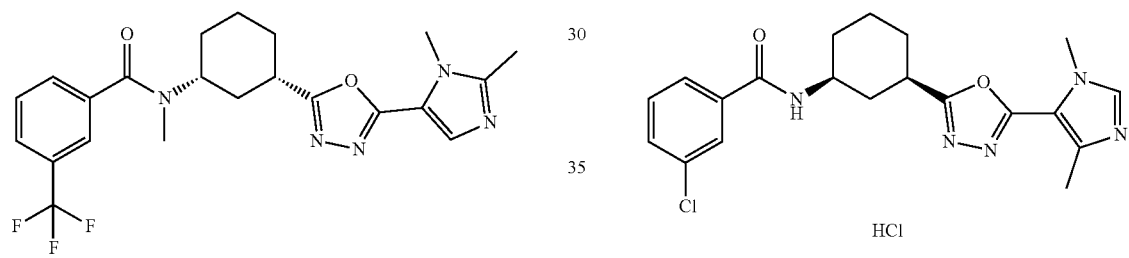

Add Burgess reagent (0.853 g, 3.474) to a mixture of N-[(1R,3S)-3-[[(2,3-dimethylimidazole-4-carbonyl)amino]carbamoyl]cyclohexyl]-N-methyl-3-(trifluoromethyl)benzamide (0.539 g, 0.868 mmol) in THF (20 mL). Stir the mixture at rt for 2.5 days and at 60° C. for 3 hrs. Concentrate the mixture and purify the residue via silica gel flash chromatography eluting with a gradient of MeOH/DCM=0-4% to give the title compound (0.498 g, 98.7%) as a light brown solid. LC/MS (m/z)=448 (M+H).

Prepare the following compound essentially as described for Preparation 22 using the appropriate hydrazide.

Add Burgess reagent (1.46 g, 5.92 mmol) to a stirring solution of cis-racemic-3-chloro-N-[3-[[(3,5-dimethylimidazole-4-carbonyl)amino]carbamoyl]cyclohexyl]benzamide (1.10 g, 2.37 mmol) in 1,2-dichloroethane (20 mL). Stir the mixture at 80° C. for 2 hrs. Add DCM (100 mL) and wash with H₂O (50 mL) and brine (50 mL). Dry the organic layer over sodium sulfate, and concentrate to dryness. Purify the crude product by prep-HPLC (column: Agela ABS C18 150*25 mm*5 μm, gradient: 20-50% B (A=water/0.05% HCl, B=ACN), flow rate: 25 mL/min) to give the title compound (0.350 g, 30.5%) as a yellow solid. LC/MS (m/z): 400 (M+H).

| Prep. | Chemical Name | Structure | ES/MS (m/z) (M + H) |
|---|---|---|---|
| 23 | Cis-chiral-N-Methyl-N-[(1R,3S)-3-[5-(2-methyl-1H-imidazol-5-yl)-1,3,4-oxadiazol-2-yl]cyclohexyl]-3-(trifluoromethyl)benzamide | 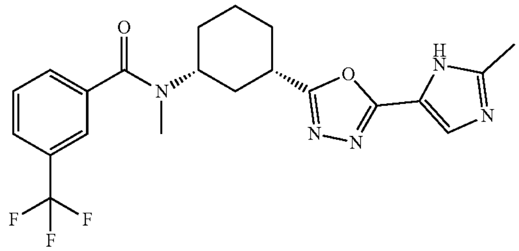 [SMILES: Cc1ncc(-c2nnc([C@H]3CCC[C@@H](N(C)C(=O)c4cccc(C(F)(F)F)c4)C3)o2)[nH]1] | 434 |

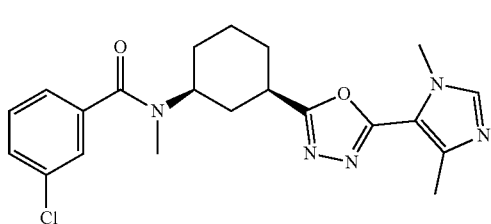 [SMILES: Cc1ncn(C)c1-c1nnc([C@@H]2CCC[C@H](N(C)C(=O)c3cccc(Cl)c3)C2)o1]
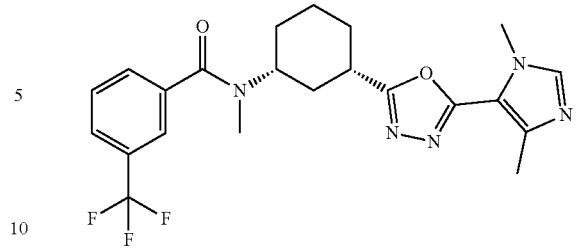

Add DiPEA (1.1 g, 8.2 mmol) to a mixture of 3-chloro-N-[(1S,3R)-3-(hydrazinecarbonyl)cyclohexyl]-N-methyl-benzamide (0.85 g, 2.7 mmol), 3,5-dimethylimidazole-4-carboxylic acid (0.42 g, 3.0 mmol), and HATU (1.6 g, 4.1 mmol) in THF (70 mL). Stir the mixture at rt for 6 hrs. Concentrate the mixture and purify the residue via silica gel flash chromatography eluting with DCM/MeOH=10/1 to give an intermediate. Dissolve the intermediate in THF (70 mL), add Burgess reagent (2.0 g, 8.2 mmol, 3.0 equiv.) and stir the mixture at rt for 4 hrs. Concentrate the mixture and purify the residue via silica gel flash chromatography eluting with a gradient of MeOH/DCM=0-10% to give the title compound (0.45 g, 40%). MS (m/z): 414 (M+1).

Add together 3-[methyl-[3-(trifluoromethyl)benzoyl]amino] cyclohexanecarboxylic acid (0.51 g, 1.47 mmol), 3,5-dimethylimidazole-4-carbohydrazide (0.28 g, 1.62 mmol), HATU (0.63 g, 1.62 mmol), DiPEA (0.57 mL, 3.24 mmol) and THF (40 mL). Stir the mixture at rt for 45 min Add Burgess reagent (1.10 g, 4.41 mmol) and stir the mixture overnight. Concentrate the mixture to dryness, dilute the residue with water and EtOAc until all is in solution, and extract with EtOAc (2×100 mL). Dry the organic extracts over MgSO$_4$, filter, and concentrated the solution to dryness. Purify the residue by silica gel flash chromatography eluting with a gradient of 0% to 4% MeOH in DCM to give the title compound (0.59 g, 85.0%) as a white solid. MS (m/z): 448 (M+1).

Prepare the following compounds essentially as described for Preparation 26 using the appropriate hydrazide and carboxylic acid.

| Prep. | Chemical Name | Structure | ES/MS (m/z) (M + H) |
|---|---|---|---|
| 27 | Cis-chiral-N-Methyl-N-[(1R,3S)-3-[5-(4-methyl-1H-imidazol-5-yl)-1,3,4-oxadiazol-2-yl]cyclohexyl]-3-(trifluoromethyl)benzamide | 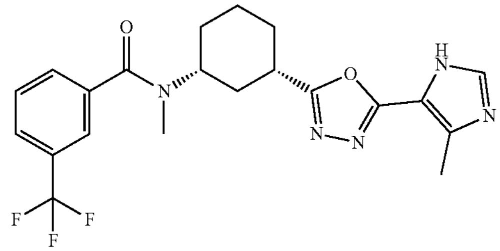 [SMILES: Cc1nc[nH]c1-c1nnc([C@H]2CCC[C@@H](N(C)C(=O)c3cccc(C(F)(F)F)c3)C2)o1] | 434 |
| 28 | Cis-chiral-N-[(1R,3S)-3-[5-(6,8-Dihydro-5H-imidazo[2,1-c][1,4]oxazin-3-yl)-1,3,4-oxadiazol-2-yl]cyclohexyl]-N-methyl-3-(trifluoromethyl)benzamide | 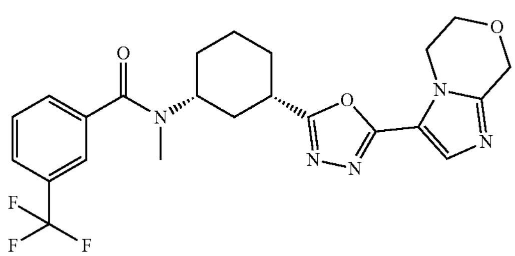 [SMILES: CN(C(=O)c1cccc(C(F)(F)F)c1)[C@@H]1CCC[C@H](c2nnc(-c3cnc4n3CCOC4)o2)C1] | 476 |
| 29 | Cis-chiral-3-Chloro-N-[(1R,3S)-3-[5-[3-(2-methoxyethyl)-5-methyl-imidazol-4-yl]-1,3,4-oxadiazol-2-yl]cyclohexyl]-N-methyl-benzamide | 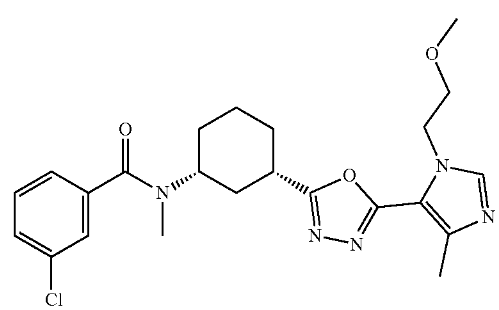 [SMILES: COCCn1cnc(C)c1-c1nnc([C@H]2CCC[C@@H](N(C)C(=O)c3cccc(Cl)c3)C2)o1] | 458 |

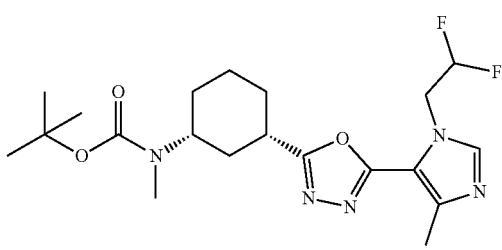 [SMILES: Cc1ncn(CC(F)F)c1-c1nnc([C@H]2CCC[C@@H](N(C)C(=O)OC(C)(C)C)C2)o1]

Add DiPEA (0.600 g, 4.55 mmol) to a mixture of (1S, 3R)-3-[tert-butoxycarbonyl(methyl)amino]cyclohexanecarboxylic acid (0.780 g, 1.82 mmol), difluoroethyl)-5-methyl-imidazole-4-carbohydrazide (0.469 g, 1.52 mmol) and HATU (0.772 g, 1.97 mmol) in THF (20 mL) and stir the mixture at rt for 1 hr. Add Burgess reagent (1.490 g, 6.06 mmol.) and stir the mixture at 70° C. for 2 days. Concentrate the mixture and dissolve the residue in water (50 mL) and EtOAc (50 mL). Extract the solution with EtOAc (3×100 mL), combine the organic extracts, dry over $Na_2SO_4$, filter, concentrate to dryness, and purify the residue via silica gel flash chromatography eluting with a gradient of EtOAc/hexane=0-85% to give the title compound (0.433 g, 41.6%, 62% purity) as a brown oil. LC/MS (m/z): 426 (M+H).

Prepare the following compound essentially as described for Preparation 30 using the appropriate acid.

| Prep. | Chemical Name | Structure | ES/MS (m/z) (M + H) |
|---|---|---|---|
| 31 | tert-Butyl N-methyl-N-[(1R,3S)-3-[5-(4-methyl-1H-imidazol-5-yl)-1,3,4-oxadiazol-2-yl]cyclohexyl]carbamate | 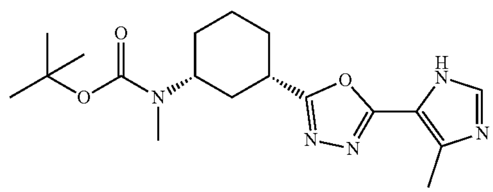 [SMILES: Cc1nc[nH]c1-c1nnc([C@H]2CCC[C@@H](N(C)C(=O)OC(C)(C)C)C2)o1] | 362 |

30

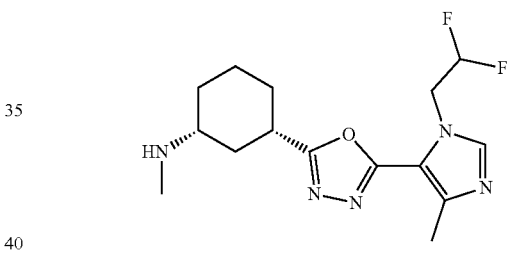

Add TFA (0.48 mL, 6.31 mmol) to a solution of tert-butyl N-[(1R,3S)-3-[5-[3-(2,2-difluoroethyl)-5-methyl-imidazol-4-yl]-1,3,4-oxadiazol-2-yl]cyclohexyl]-N-methyl-carbamate (0.433 g, 0.631 mmol) in DCM (3 mL). Stir the mixture at rt for 1 hr. Add water (5 mL) and adjust the pH to 9-10 with NaOH (4 M) solution. Concentrate the mixture to dryness to give the title compound (0.631 mmol, 100.0%) as a yellow solid. LC/MS (m/z): 326 (M+H).

Prepare the following compound essentially as described for Preparation 32 using the appropriate carbamate.

| Prep. | Chemical Name | Structure | ES/MS (m/z) (M + H) |
|---|---|---|---|
| 33 | (1R,3S)-N-Methyl-3-[5-(4-methyl-1H-imidazol-5-yl)-1,3,4-oxadiazol-2-yl]cyclohexanamine | 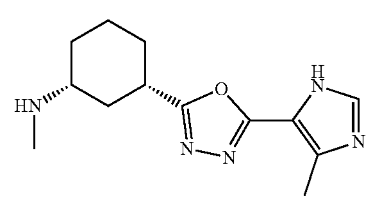 [SMILES: CN[C@@H]1CCC[C@H](c2nnc(-c3[nH]cnc3C)o2)C1] | 262 |

23

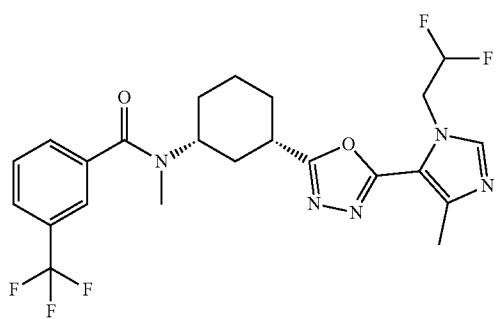 [SMILES: Cc1ncn(CC(F)F)c1-c1nnc([C@H]2CCC[C@@H](N(C)C(=O)c3cccc(C(F)(F)F)c3)C2)o1]

24

Add TEA (0.44 mL, 3.155 mmol) and 3-(trifluoromethyl)benzoyl chloride (0.145 g, 0.694 mmol) to a solution of (1R,3S)-3-[5-[3-(2,2-difluoroethyl)-5-methyl-imidazol-4-yl]-1,3,4-oxadiazol-2-yl]-N-methyl-cyclohexanamine (0.631 mmol) in DCM (15 mL). Stir the reaction at rt for 1.5 hrs. Concentrate the mixture and purify the residue via silica gel flash chromatography eluting with a gradient of MeOH/DCM=0-5% to give the title compound (0.522 g, 83.2%, 50% purity) as a yellow oil. LC/MS (m/z): 498 (M+H).

Prepare the following compound essentially as described for Preparation 34 using the appropriate cyclohexanamine.

| Prep. | Chemical Name | Structure | ES/MS (m/z) (M + H) |
|---|---|---|---|
| 35 | N-Methyl-N-[(1R,3S)-3-[5-(4-methyl-1H-imidazol-5-yl)-1,3,4-oxadiazol-2-yl]cyclohexyl]-3-(trifluoromethoxy)benzamide | 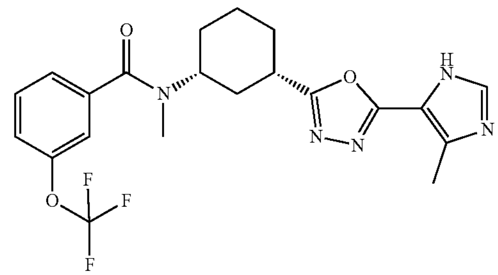 [SMILES: Cc1nc[nH]c1-c1nnc([C@H]2CCC[C@@H](N(C)C(=O)c3cccc(OC(F)(F)F)c3)C2)o1] | 450 |

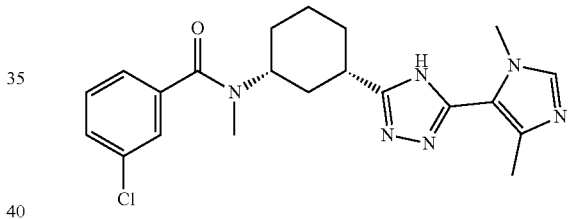

Heat a mixture of 3-chloro-N-[(1R,3S)-3-[5-(3,5-dimethylimidazol-4-yl)-1,3,4-oxadiazol-2-yl]cyclohexyl]-N-methyl-benzamide (0.630 g, 1.52 mmol) and ammonium acetate (1.53 g, 13 equiv., 19.8 mmol) in acetic acid (8 mL) under microwave conditions (160° C.) for 5 hrs. Concentrate the mixture to provide a residue. Subject the residue to silica gel flash chromatography eluting with MeOH/DCM/TEA=1/10/0.01. Collect the desired fractions containing the title compound. Further subject the title compound to prep-HPLC eluting with a gradient of 9-24% ACN in water (0.1% formic acid) to give the title compound (176 mg, 28.1%, ee 99%). MS (m/z): 413 (M+1).

Prepare the following compounds essentially as described for Example 1 using the appropriate oxadiazole.

| Ex. No. | Chemical Name | Structure | ES/MS (m/z) (M + H) |
|---|---|---|---|
| 2 | Cis-chiral-3-Chloro-N-methyl-N-[(1R,3S)-3-[5-(4-methyl-1H-imidazol-5-yl)-4H-1,2,4-triazol-3-yl]cyclohexyl]benzamide | 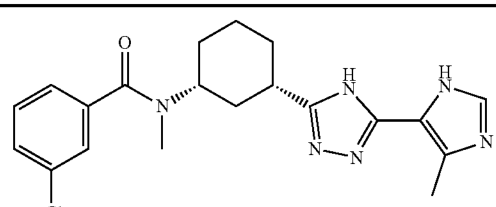 | 399 |

| Ex. No. | Chemical Name | Structure | ES/MS (m/z) (M + H) |
|---|---|---|---|
| 3 | Cis-chiral-3-Chloro-N-[(1R,3S)-3-[5-(2,3-dimethylimidazol-4-yl)-4H-1,2,4-triazol-3-yl]cyclohexyl]-N-methyl-benzamide | 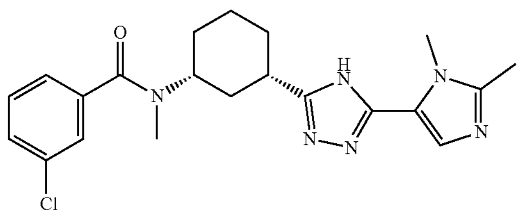 [SMILES: Cc1ncc(-c2nnc([C@H]3CCC[C@@H](N(C)C(=O)c4cccc(Cl)c4)C3)[nH]2)n1C] | 413 |

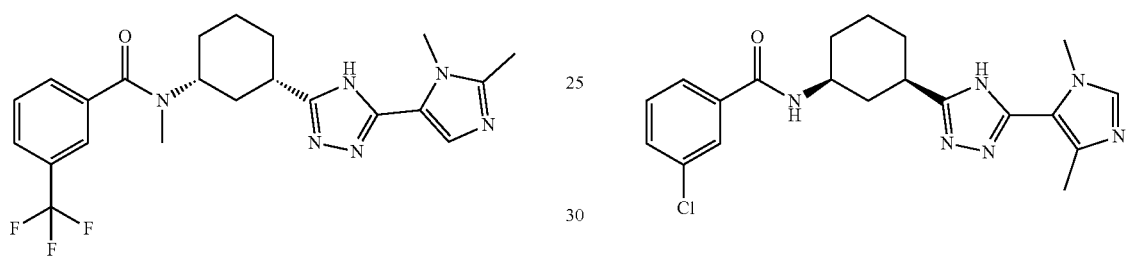

Heat a mixture of N-[(1R,3S)-3-[5-(2,3-dimethylimidazol-4-yl)-1,3,4-oxadiazol-2-yl]cyclohexyl]-N-methyl-3-(trifluoromethyl)benzamide (0.498 g, 0.857 mmol) and ammonium acetate (0.661 g, 8.571 mmol) in acetic acid (3.0 mL) under microwave conditions at 160° C. for 10 hrs. Concentrate the mixture and purify the residue via silica gel flash chromatography, eluting with MeOH/DCM=0-4%. Further purify the material with prep-HPLC (Agilent 1260 Infinity, column, XBridge C18 5μ 30*150 mm, mobile phase: A: water (10 mM NH₄HCO₃), B:ACN) to give the title compound (0.0876 g, 22.4%) as a white solid. LC/MS (m/z): 447 (M+1).

Prepare the following compound essentially as described for Example 4 using the appropriate oxadiazole.

Add ammonium acetate (0.620 g, 8.04 mmol) to a stirring solution of cis-racemic-3-chloro-N-[3-[5-(3,5-dimethylimidazol-4-yl)-1,3,4-oxadiazol-2-yl]cyclohexyl]benzamide;hydrochloride (300 mg, 0.619 mmol) in acetic acid (5 mL). Heat the reaction under microwave conditions at 160° C. for 3 hrs. Concentrate the mixture and adjust the pH to 10 with a saturated Na₂CO₃ solution. Extract the aqueous with DCM (4×50 mL). Combine the organic extracts, wash with brine (80 mL), dry over Na₂SO₄, filter, and concentrate the filtrate to dryness to give the crude product. Purify the crude product by prep-HPLC (column: DuraShell 150*25 mm*5 μm, gradient: 30-55% B (A=water/0.05% ammonia hydroxide, B=ACN), flow rate: 30 mL/min) to give the title compound (25.1 mg, 10.1%) as a white solid. LC/MS (m/z): 399 (M+H).

| Ex. No. | Chemical Name | Structure | ES/MS (m/z) (M + H) |
|---|---|---|---|
| 5 | Cis-chiral-N-Methyl-N-[(1R,3S)-3-[5-(2-methyl-1H-imidazol-5-yl)-4H-1,2,4-triazol-3-yl]cyclohexyl]-3-(trifluoromethyl)benzamide | 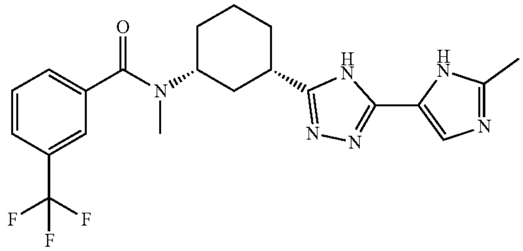 [SMILES: Cc1ncc(-c2nnc([C@H]3CCC[C@@H](N(C)C(=O)c4cccc(C(F)(F)F)c4)C3)[nH]2)[nH]1] | 433 |

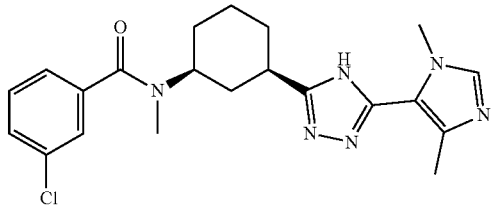 [SMILES: Cc1ncn(C)c1-c1nnc([C@@H]2CCC[C@H](N(C)C(=O)c3cccc(Cl)c3)C2)[nH]1]

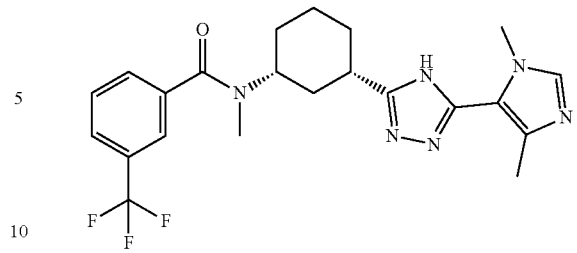

Heat a mixture of 3-chloro-N-[(1S,3R)-3-[5-(3,5-dimethylimidazol-4-yl)-1,3,4-oxadiazol-2-yl]cyclohexyl]-N-methyl-benzamide (0.30 g, 0.72 mmol) and ammonium acetate (0.73 g, 9.4 mmol) in acetic acid (8 mL, 139.6 mmol) under microwave conditions at 160° C. for 5 hrs. Concentrate the mixture and purify the residue via silica gel flash chromatography eluting with MeOH/DCM/TEA=1/10/0.01 followed by a further purification with prep-HPLC eluting with 23-33% ACN in water (10 mM NH$_4$HCO$_3$) to give the title compound (50 mg, 17%). MS (m/z): 413 (M+1).

Add together N-[3-[5-(3,5-dimethylimidazol-4-yl)-1,3,4-oxadiazol-2-yl]cyclohexyl]-N-methyl-3-(trifluoromethyl)benzamide (590 mg, 1.25 mmol), 4 Å molecular sieves (100 mg), ammonium acetate (0.96 g, 12.53 mmol) and acetic acid (10 mL). Heat the mixture at 150° C. under microwave conditions for 5 hrs. Concentrate the mixture and purify the residue by silica gel flash chromatography eluting with a gradient of 0% to 4% MeOH in DCM followed by a further purification with reverse phase flash chromatography eluting with 20-40% ACN in water (10 mM NH$_4$HCO$_3$) to give the title compound (113 mg, 19.8%) as a white solid. MS (m/z): 447 (M+1).

Prepare the following compounds essentially as described for Example 8 using the appropriate oxadiazole.

| Ex. No. | Chemical Name | Structure | ES/MS (m/z) (M + H) |
|---|---|---|---|
| 9 | Cis-chiral-N-Methyl-N-[(1R,3S)-3-[5-(4-methyl-1H-imidazol-5-yl)-4H-1,2,4-triazol-3-yl]cyclohexyl]-3-(trifluoromethyl)benzamide | 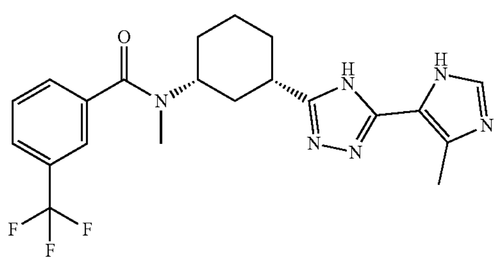 [SMILES: Cc1nc[nH]c1-c1nnc([C@H]2CCC[C@@H](N(C)C(=O)c3cccc(C(F)(F)F)c3)C2)[nH]1] | 433 |
| 10 | Cis-chiral-N-[(1R,3S)-3-[5-(6,8-Dihydro-5H-imidazo[2,1-c][1,4]oxazin-3-yl)-4H-1,2,4-triazol-3-yl]cyclohexyl]-N-methyl-3-(trifluoromethyl)benzamide | 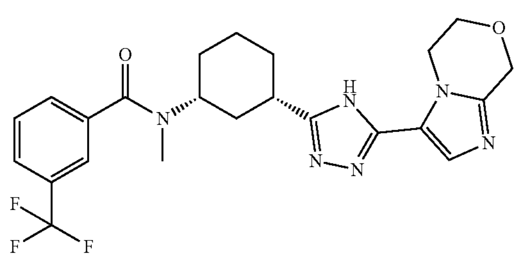 [SMILES: CN(C(=O)c1cccc(C(F)(F)F)c1)[C@@H]1CCC[C@H](c2nnc(-c3cnc4n3CCOC4)[nH]2)C1] | 475 |
| 11 | Cis-chiral-3-Chloro-N-[(1R,3S)-3-[5-[3-(2-methoxyethyl)-5-methyl-imidazol-4-yl]-4H-1,2,4-triazol-3-yl]cyclohexyl]-N-methyl-benzamide | 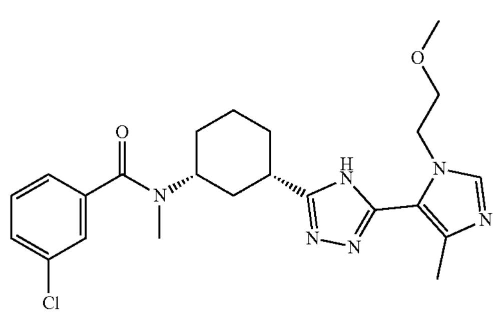 [SMILES: COCCn1cnc(C)c1-c1nnc([C@H]2CCC[C@@H](N(C)C(=O)c3cccc(Cl)c3)C2)[nH]1] | 457 |

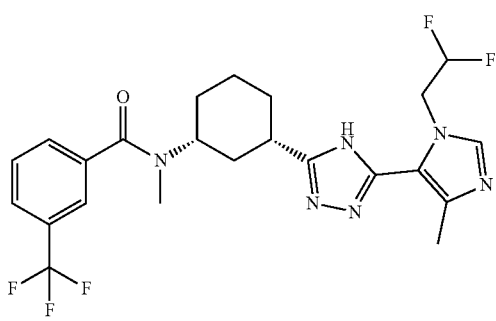 [SMILES: Cc1ncn(CC(F)F)c1-c1nnc([C@H]2CCC[C@@H](N(C)C(=O)c3cccc(C(F)(F)F)c3)C2)[nH]1]

Heat a mixture of N-[(1R,3S)-3-[5-[3-(2,2-difluoroethyl)-5-methyl-imidazol-4-yl]-1,3,4-oxadiazol-2-yl]cyclohexyl]-N-methyl-3-(trifluoromethyl)benzamide (0.522 g, 0.525 mmol) and ammonium acetate (0.404 g, 5.25 mmol) in acetic acid (3 mL) at 160° C. under microwave conditions for 16 hrs. Concentrate the mixture and purify the residue with prep-HPLC (Gilson 281, column: SunFire C18 5μ 30*100 mm, mobile phase: A: water (0.1% FA), B: ACN (0.1% FA)) to give the title compound (0.016 g, 6.0%) as a white solid. LC/MS (m/z): 497 (M+H).

Prepare the following compound essentially as described for Example 12 using the appropriate oxadiazole.

than 120 nM hGPR142 IP1 $EC_{50}$ (nM) with an efficacy of 120%. Example 1 exhibited an $EC_{50}$ of 14.4 nM (n=3) hGPR142 IP1 with a relative efficacy of 110%±5, n=3.

These results indicate that the compounds of Formula 1 are effective to modulate GPR142.

Intraperitoneal Glucose Tolerance Tests (IPGTT)

The IPGTT assay is used to examine the ability of a compound to activate GPR142 in vivo resulting in anti-diabetic efficacy, i.e. reduction in plasma glucose levels. Male C57BL/6 mice (8-10 weeks of age) are fed normal rodent chow diet and water ad libitum. On the night before the study, fast the animals overnight in clean cages. On the morning of the study, orally dose the animals with either vehicle or a test compound at the indicated doses 90 min prior to the glucose challenge (2 g/kg) by intraperitoneal injection. Determine the blood glucose levels from tail bleeds taken immediately prior to compound dosing (−90 min) and 0, 15, 30, and 60 min after glucose challenge using handheld glucometers. Use the blood glucose profile from t=0 to t=60 min to calculate an area under the curve (AUC) for each treatment. Calculate the percent glucose lowering. The AUC is calculated for each treatment group with respect to the AUC of vehicle group. A compound with a reduction in glucose AUC (P<0.05) is considered positive in the assay.

The Compound of Example 1 is tested essentially as described above, compared to control, and exhibited $ED_{50}$ of 0.25 (mpk)

| Ex. No. | Chemical Name | Structure | ES/MS (m/z) (M + H) |
|---|---|---|---|
| 13 | N-Methyl-N-[(1R,3S)-3-[5-(4-methyl-1H-imidazol-5-yl)-4H-1,2,4-triazol-3-yl]cyclohexyl]-3-(trifluoromethoxy)benzamide | 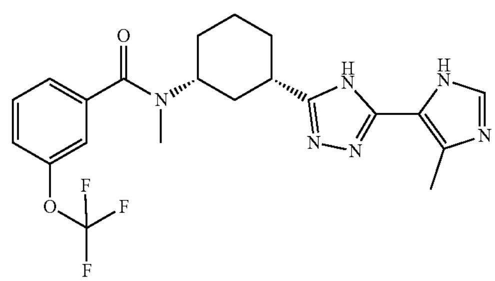 [SMILES: Cc1nc[nH]c1-c1nnc([C@H]2CCC[C@@H](N(C)C(=O)c3cccc(OC(F)(F)F)c3)C2)[nH]1] | 449 |

Biological Assays

GPR142 Agonist Effect as Measured by IP-1 Assay

HEK293 cells expressing human GPR142 are maintained in DMEM supplemented with 10% FBS and 800 μg/ml G418 (Geneticin®) at 37° C. and 5% $CO_2$. Plate the cells in 384 well plates at 5000 cells per well and allow 18 hrs for attachment. Add the test compound at varying concentrations ranging from 30 μM to 1 nM. Incubate the cells for 1 hr. IP-1 measurements are performed using an IP-One HTRF® assay kit (Cisbio) according to manufacturer's protocol using an assay buffer containing 1×HBSS (+Ca, +Mg), 0.1% BSA, 50 mM LiCl and 20 mM HEPES, pH 7.2. Stop the reaction by the addition of IP1-d2 (IP-1 coupled to an organic HTRF acceptor) followed by cryptate solution (http://www.htrf.com/usa/htrf-chemistry). Incubate the plates at 25° C. for 1 hr. Read the fluorescence in an Envision instrument at 665 nm and 620 nm wavelength. Calculate the ratio of 665 nm/620 nm fluorescence and convert to IP-1 levels using an IP-1 standard curve. The data is fit to a 4 parameter-fit logistics to determine $EC_{50}$ values. The compounds of the Examples compounds are tested essentially as described above and exhibit $EC_{50}$ values less The compound of Example 1 is considered positive in the assay and activating GPR142 in vivo resulting in anti-diabetic activity.

What is claimed is:

1. A compound of the formula below,

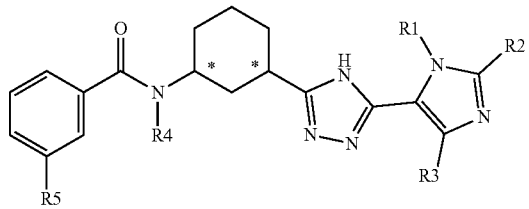

wherein * designates a chiral center;

R1 is selected from: H, —$CH_3$, —$CH_2CH_2OCH_3$, and —$CH_2CHF_2$;

R2 is selected from H and CH$_3$, or R1 and R2 can join to from a fused 6 membered heterocyclic ring containing O and the N bonded to 4R1;
R3 is H or —CH$_3$;
R4 is H or —CH$_3$; and
R5 is selected from: Cl, —CF$_3$, and —OCF$_3$; or
a pharmaceutically acceptable salt thereof.

2. A compound as claimed by claim 1 wherein the compound is of the formula below, or a pharmaceutically acceptable salt thereof:

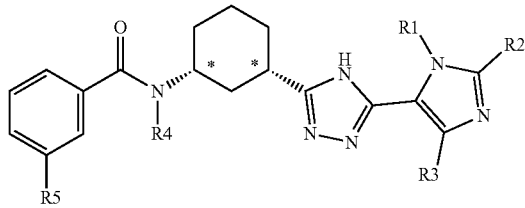

wherein * designates a chiral center and the substituents attached to the chiral centers are cis relative to each other;
R1 is selected from: H, —CH$_3$, —CH$_2$CH$_2$OCH$_3$, and —CH$_2$CHF$_2$;
R2 is selected from H and CH$_3$, or R1 and R2 can join to from a fused 6 membered heterocyclic ring containing 0 and the N bonded to R1;
R3 is H or —CH$_3$;
R4 is H or —CH$_3$; and
R5 is selected from Cl, —CF$_3$, and —OCF$_3$.

3. A compound according to claim 1 or a pharmaceutically acceptable salt thereof, wherein R1 is selected from: —CH$_3$, —CH$_2$CH$_2$OCH$_3$, and —CH$_2$CHF$_2$.

4. A compound according to claim 1, or a pharmaceutically acceptable salt thereof, wherein R1 is selected from —CH$_3$, —CH$_2$CH$_2$OCH$_3$, —CH$_2$CHF$_2$.

5. A compound according to claim 1, or a pharmaceutically acceptable salt thereof, wherein R1 is —CH$_3$.

6. A compound according to claim 1, or a pharmaceutically acceptable salt thereof, wherein R1 and R2 combine to form a fused 6 membered heterocyclic ring containing O and the N attached to R1.

7. A compound according to claim 1, or a pharmaceutically acceptable salt thereof, wherein R2 is H.

8. A compound according to claim 1, or a pharmaceutically acceptable salt thereof, wherein R3 is —CH$_3$.

9. A compound according to claim 1, or a pharmaceutically acceptable salt thereof, wherein R4 is —CH$_3$.

10. A compound according to claim 1 wherein R5 is Cl or —OCF$_3$.

11. A compound as claimed by claim 1 wherein the compound is of the formula:

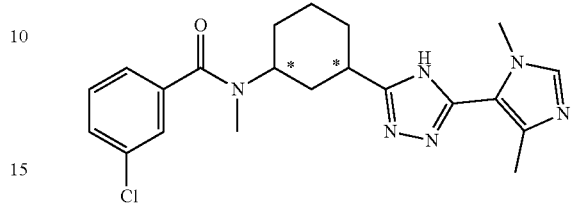

wherein * designates a chiral center, or a pharmaceutically acceptable salt thereof.

12. A compound as claimed by claim 1 wherein the compound is of the formula:

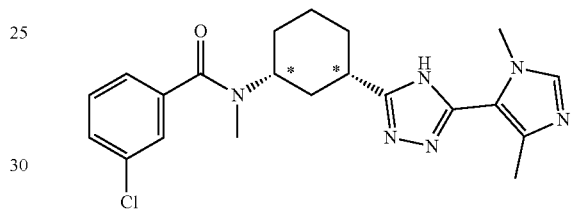

wherein * designates a chiral center and the substituents attached to the chiral centers are cis relative to each other, or pharmaceutically acceptable salt thereof.

13. A pharmaceutical composition comprising a compound according to claim 1, or a pharmaceutically acceptable salt thereof, and at least one of a pharmaceutically acceptable carrier, diluent, or excipient.

14. A pharmaceutical composition comprising a compound according to claim 11, or a pharmaceutically acceptable salt thereof and at least one of a pharmaceutically acceptable carrier, diluent, or excipient.

15. A method for treating a patient in need of treatment for type II diabetes, comprising administering to the patient an effective amount of a compound according to claim 1.

* * * * *